United States Patent
Shieh et al.

(10) Patent No.: US 10,912,843 B2
(45) Date of Patent: Feb. 9, 2021

(54) ENDOPLASMIC RETICULUM-TARGETING NANOVEHICLES AND METHODS FOR USE THEREOF

(71) Applicant: National Cheng Kung University, Tainan (TW)

(72) Inventors: Chi-Chang Shieh, Tainan (TW); Chia-Liang Yen, Tainan (TW); Dar-Bin Shieh, Tainan (TW); Si-Tse Jiang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 16/263,618

(22) Filed: Jan. 31, 2019

(65) Prior Publication Data
US 2019/0307894 A1 Oct. 10, 2019

Related U.S. Application Data

(60) Provisional application No. 62/652,502, filed on Apr. 4, 2018.

(51) Int. Cl.

| | |
|---|---|
| A61K 47/69 | (2017.01) |
| A61K 36/9066 | (2006.01) |
| A61K 47/59 | (2017.01) |
| A61P 37/00 | (2006.01) |
| A01K 67/027 | (2006.01) |
| A61K 9/00 | (2006.01) |
| A61K 36/06 | (2006.01) |
| A61K 36/22 | (2006.01) |
| A61K 36/23 | (2006.01) |
| A61K 36/9062 | (2006.01) |
| A61K 31/05 | (2006.01) |
| A61K 31/365 | (2006.01) |
| A61K 31/55 | (2006.01) |
| A61K 31/407 | (2006.01) |
| A61K 45/06 | (2006.01) |
| A61K 31/12 | (2006.01) |
| A61K 31/58 | (2006.01) |
| A61P 43/00 | (2006.01) |
| A61K 31/7048 | (2006.01) |

(52) U.S. Cl.
CPC ...... *A61K 47/6925* (2017.08); *A01K 67/0275* (2013.01); *A01K 67/0278* (2013.01); *A61K 9/0056* (2013.01); *A61K 31/05* (2013.01); *A61K 31/12* (2013.01); *A61K 31/365* (2013.01); *A61K 31/407* (2013.01); *A61K 31/55* (2013.01); *A61K 31/58* (2013.01); *A61K 31/7048* (2013.01); *A61K 36/06* (2013.01); *A61K 36/22* (2013.01); *A61K 36/23* (2013.01); *A61K 36/9062* (2013.01); *A61K 36/9066* (2013.01); *A61K 45/06* (2013.01); *A61K 47/593* (2017.08); *A61P 37/00* (2018.01); *A61P 43/00* (2018.01); *A01K 2217/075* (2013.01); *A01K 2217/206* (2013.01); *A01K 2227/105* (2013.01); *A01K 2267/0306* (2013.01)

(58) Field of Classification Search
None
See application file for complete search history.

(56) References Cited

U.S. PATENT DOCUMENTS

| 9,137,411 B2 | 9/2015 | Ranjan et al. |
|---|---|---|
| 9,168,307 B2 | 10/2015 | Anderson et al. |
| 9,555,011 B2 | 1/2017 | Braden et al. |
| 2008/0025921 A1 | 1/2008 | Caplan et al. |
| 2013/0045162 A1 | 2/2013 | Lillard, Jr. et al. |
| 2016/0175265 A1 | 6/2016 | Duvall et al. |

FOREIGN PATENT DOCUMENTS

WO  WO-03/049717 A2  6/2003

OTHER PUBLICATIONS

Yen et al.,"Poly Lactic-co-glycolic acid nanoparticles encapsulation enhance the effectiveness of curcumin for rescuing trafficking-defective gp91phox in chronic granulomatous disease leukocytes", J Immunol, May 1, 2017, 198 (Year: 2017).*

Wang et al., "KDEL peptide gold nanoconstructs: promising nanoplatforms for drug delivery", Nanomedicine: Nanotechnology, Biology and Medicine, 2013, pp. 366-374 (Year: 2013).*

Cartiera et al., "Partial Correction of Cystic Fibrosis Defects with PLGA Nanoparticles Encapsulating Curcumin", Molecular Pharmaceutics, Nov. 2009, pp. 86-93 (Year: 2009).*

(Continued)

*Primary Examiner* — Lianko G Garyu (74) *Attorney, Agent, or Firm* — Cesari & McKenna, LLP (57) ABSTRACT

A method for treating a disease caused by protein retention in the endoplasmic reticulum (ER) with a sarcoplasmic/endoplasmic reticulum calcium ATPase pump inhibitor encapsulated in a polymer nanoparticle. The polymer nanoparticle is surface-modified such that it is targeted to the ER. The inhibitor reduces protein retention in the ER and the encapsulation lowers side effects of the inhibitor, e.g., cytotoxicity, as compared to administering the inhibitor without encapsulation. Also disclosed is a pharmaceutical composition that can be used for carrying out the method. Further provided is a transgenic mouse carrying in its genome a heterologous nucleic acid that encodes an H338Y mutant gp91$^{phox}$ protein. The transgenic mouse can serve as a model for human chronic granulomatous disease.

7 Claims, 5 Drawing Sheets

Specification includes a Sequence Listing.

(56) References Cited

OTHER PUBLICATIONS

Merriam-Webster, "side effect", obtained from https://www.learnersdictionary.com/definition/side%20effect on Aug. 31, 2020 (Year: 2020).*

Chen et al "The Endoplasmic Reticulum Stress Inducer Thapsigargin Enhances the Toxicity of ZnO Nanoparticles to Macrophages and Macrophage-Endothelial Co-Culture" Environmental Toxicology and Pharmacology vol. 50, pp. 103-110, 2017.

Huang et al "Thapsigargin and Flavin Adenine Dinucleotide Ex Vivo Treatment Rescues Trafficking-Defective Gp91phox in Chronic Granulomatous Disease Leukocytes" Free Radical Biology and Medicine vol. 47, pp. 932-940, 2009.

Peng et al "Curcumin-Loaded Nanoparticles Enhance Apoptotic Cell Death of U2OS Human Osteosarcoma Cells Through the Akt-Bad Signaling Pathway" International Journal of Oncology vol. 44, pp. 238-246, 2014.

Yen et al "Poly Lactic-Co-Glycolic Acid Nanoparticles Encapsulation Enhance the Effectiveness of Curcumin for Rescuing Trafficking-Defective Gp91phox in Chronic Granulomatous Disease Leukocytes" Journal of Immunology vol. 198, p. 81.12, 2017.

* cited by examiner

ENDOPLASMIC RETICULUM-TARGETING NANOVEHICLES AND METHODS FOR USE THEREOF

CROSS-REFERENCE TO RELATED APPLICATIONS

This application claims priority of U.S. Provisional Patent Application No. 62/652,502, filed on Apr. 4, 2018.

BACKGROUND

Chronic granulomatous disease (CGD) is a primary immunodeficiency disease caused by defects in nicotinamide adenine dinucleotide phosphate oxidase 2 (NOX2) in leukocytes. See, e.g., Holland 2013, Hematol. Oncol. Clin. North Am. 27:89-99; O'Neill et al. 2015, Redox Biol. 6:135-156; and Roos 2016, Br. Med. Bull. 118:50-63(Roos). NOX2 is composed of membrane-bound subunits $gp91^{phox}$ and $p22^{phox}$, as well as cytosolic components $p40^{phox}$, $p47^{phox}$, $p67^{phox}$, and small GTPase Rac1/2. See Roos. CGD patients carrying a mutation in a gene encoding one of the NOX2 component proteins are susceptible to various infections and certain autoimmune diseases due to lack of NOX2-mediated reactive oxygen species (ROS) production by activated leukocytes. See Huang et al. 2016, Inflamm. Bowel Dis. 22:2794-280; Huang et al. 2015, Antioxid. Redox Signal. 23:973-984; and Nguyen et al. 2017, Front. Cell Infect. Microbiol. 7:373.

A CGD patient has been identified with a point mutation in the Cybb gene, which encodes $gp91^{phox}$. See Lin et al. 2002, Biochim. Biophys. Acta 1586:275-286 (Lin). The mutated Cybb gene $Cybb^{C1024T}$ produces a mutant $gp91^{phox}$ protein containing a single amino acid change, designated as H338Y-$gp91^{phox}$. H338Y-$gp91^{phox}$ exists in an immature form that is retained in the endoplasmic reticulum (ER) and subsequently degraded by the protein quality control machinery in the ER. See Id.

A sarcoplasmic/endoplasmic reticulum calcium ATPase (SERCA) inhibitor, namely, thapsigargin, has been previously shown to rescue ER retention of H338Y-$gp91^{phox}$ in CGD leukocytes and restore leukocyte function. See Huang et al. 2009, Free Radical Biol. Med. 47:932-940. Curcumin, also a SERCA inhibitor, has been shown to partially correct aberrant ER protein retention in cystic fibrosis. See Egan et al. 2004, Science 304:600-602. Yet, curcumin has cytotoxic side effects including ER stress and apoptosis. See Gupta et al. 2013, Mol. Nutr. Food Res. 57:1510-1528; Liu et al. 2016, Evid. Based Complement. Alternat. Med. 2016: 7831282; and Reuter et al. 2008, Biochemical Pharmacology 76:1340-1351.

The need exists to develop pharmaceutical compositions and methods for treating diseases of ER retention that have greater efficacy and fewer side-effects.

SUMMARY

To meet the need discussed above, a method is disclosed for treating a disease caused by protein retention in the endoplasmic reticulum. The method is carried out by obtaining a sarcoplasmic/endoplasmic reticulum calcium ATPase (SERCA) pump inhibitor encapsulated in a polymer nanoparticle and administering an effective amount of the inhibitor to a subject suffering from the disease.

The polymer nanoparticle is surface-modified such that it is targeted to the endoplasmic reticulum (ER). Further, the effective amount of the inhibitor reduces protein retention in the ER, and the encapsulation lowers side effects of the inhibitor, e.g., cytotoxicity, as compared to administering the inhibitor without encapsulation.

Also disclosed is a pharmaceutical composition that can be used for carrying out the method above. The pharmaceutical composition contains a SERCA pump inhibitor encapsulated in a polymer nanoparticle and a pharmaceutically acceptable carrier. As mentioned above, the polymer nanoparticle is surface-modified such that it is targeted to the endoplasmic reticulum.

Further, provided is a transgenic mouse carrying in its genome a heterologous nucleic acid that encodes an H338Y mutant $gp91^{phox}$ protein. The mutant $gp91^{phox}$ is expressed in cells of the transgenic mouse and wild-type $gp91^{phox}$ is not expressed in cells of the transgenic mouse. The transgenic mouse can serve as a model for human chronic granulomatous disease.

The details of one or more embodiments of the invention are set forth in the description below. Other features, objects, and advantages of the invention will be apparent from the description, the drawings, and from the claims.

BRIEF DESCRIPTION OF THE DRAWINGS

The description below refers to the accompanying drawings, of which.

DETAILED DESCRIPTION

As mentioned above, a method is disclosed for treating a disease caused by protein retention in the endoplasmic reticulum with a SERCA pump inhibitor. The inhibitor is a dietary polyphenolic compound. The compound can be, but is not limited to curcumin, thapsigargin, cyclopiazonic acid, 2, 5-di-tert-butylhydroquinone, gingerol, 7-chloro-5-(2-chlorophenyl)-1,5-dihydro-4,1-benzothiazepin2(3H)-one (CGP371571), tert-butylhydroquinone, paxilline, and saikosaponin-d. Combinations of one or more of these compounds can also be used. In a specific method, the dietary polyphenolic compound is curcumin.

The SERCA pump inhibitor is encapsulated in a polymer nanoparticle. Exemplary polymers that can be used to form the nanoparticle include poly(lactic-co-glycolic acid), poly (lactide), poly(amino acids), poly(ε-caprolactone), polyalkylcyanoacrylate, alginate, gelatin, lecithin-chitosan, albumin, and chitosan. Mixtures of these polymers can also be used. In one particular method, the polymer is formed of poly(lactic-co-glycolic acid).

The polymer nanoparticle mentioned above is surface-modified to target it to the ER. The surface modification can be an ER targeting peptide conjugated to the polymer. One or more ER targeting peptide, e.g., KDEL (SEQ ID NO: 1), KKXX (SEQ ID NO: 2), or an arginine-based RXR-type ER-retention/retrieval signal peptide, can be conjugated to the polymer. KDEL is used as the ER targeting peptide in an exemplary method.

The SERCA pump inhibitor encapsulated in the polymer nanoparticle is administered to the subject suffering from the ER retention-mediated disease in an amount effective for treating the disease. The effective amount of the inhibitor reduces protein retention in the ER, and the encapsulation lowers side effects of the inhibitor, as compared to administering the inhibitor without encapsulation. The side effects that are reduced can be cytotoxicity, e.g., ER stress and apoptosis.

The effective amount of SERCA pump inhibitor can enhance reactive oxygen species generation by leukocytes in the subject, and enhance peritoneal bacterial clearance mediated by the leukocytes.

The method described herein, as set forth above, is used for treating a disease caused by protein retention in the endoplasmic reticulum. Such diseases include, but are not limited to, chronic granulomatous disease, cystic fibrosis, hereditary emphysema, hereditary hemochromatosis, oculocutaneous albinism, protein C deficiency, type I hereditary angioedema, Fabry disease, Tay-Sachs disease, congenital sucrase-isomaltase deficiency, Crigler-Najjar type 2, diabetes mellitus, Laron syndrome, primary hypothyroidism, congenital long QT syndrome, thyroxine binding globulin deficiency, 3-thalassemia/Hb E disease, familial hypercholesterolemia, familial chylomicronemia, abeta-lipoproteinemia, congenital hypothyroidism, osteogenesis imperfecta, osteopetrosis, hereditary hypofibrinogenemia, nephrogenic diabetes insipidus, neurohypophyseal diabetes insipidus, Charcot-Marie-Tooth disease, Pelizaeus-Merzbacher disease, Alzheimer's disease, von Willebrand disease type IIA, Tangier disease, and hereditary hemorrhagic telangiectasia (HHT) type 2 with ALK1 missense mutation. In a particular method, the disease is chronic granulomatous disease.

In yet another specific method, the disease is chronic granulomatous disease, the dietary polyphenolic compound is curcumin, the polymer is poly(lactic-co-glycolic acid), and the surface modification includes ER targeting peptide KDEL conjugated to the polymer.

To carry out the above method, a pharmaceutical composition is provided. The pharmaceutical composition has the components mentioned above, together with a pharmaceutically acceptable carrier. More specifically, the composition includes a SERCA pump inhibitor encapsulated in a polymer nanoparticle, wherein the polymer nanoparticle is surface-modified such that it is targeted to the endoplasmic reticulum.

Further, the polymer nanoparticle is formed of one or more of poly(lactic-co-glycolic acid), poly(lactide), poly (amino acids), poly (ε-caprolactone), polyalkylcyanoacrylate, alginate, gelatin, lecithin-chitosan, albumin, or chitosan. The SERCA pump inhibitor is a dietary polyphenolic compound selected from the group consisting of curcumin, thapsigargin, cyclopiazonic acid, 2,5-di-tert-butylhydroquinone, gingerol, CGP37157, tert-butylhydroquinone, paxilline, and saikosaponin-d, or a combination thereof. The surface modification includes an ER targeting peptide conjugated to the polymer and the ER targeting peptide is KDEL, KKXX, or an arginine-based RXR-type ER-retention/retrieval signal.

An exemplary pharmaceutical composition contains curcumin encapsulated in a poly(lactic-co-glycolic acid) nanoparticle surface-modified with KDEL together with a pharmaceutically acceptable carrier.

As mentioned above a transgenic mouse falls within the scope of the invention. The transgenic mouse, including in its genome a heterologous nucleic acid that encodes an H338Y mutant gp91$^{phox}$ protein, expresses mutant gp91$^{phox}$ in its cells. In an example, the cells that express H338Y mutant gp91$^{phox}$ protein are leukocytes. The transgenic mice are deficient in peritoneal bacterial clearance. In particular, peritoneal bacterial clearance is reduced in the transgenic mice as compared to wild-type mice.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are herein incorporated by reference in their entirety.

EXAMPLES

Example 1: Production of CGD Transgenic Mouse

A transgenic mouse model for chronic granulomatous disease (CGD) caused by H338Y mutant gp91$^{phox}$ was established in a Cybb knock-out background as follows. A bacterial artificial chromosome (BAC) containing the murine Cybb gene (clone number RP23-210P9) was obtained from the BACPAC resource center at Children's Hospital Oakland Research Institute (Oakland, Calif. USA). The BAC was modified to contain the mutant Cybb$^{C1024T}$ using Counter Selection BAC Modification Kit (Gene Bridges, GmbH). The resultant Cybb$^{C1024T}$ BAC transgene was introduced via pronuclear injection into ova isolated from Cybb targeted mutant B6.129S-Cybb$^{tm1Din}$/J mice (Jackson Labs Cat. No. 002365) using standard techniques.

Founders and progenies carrying the BAC transgene were identified by PCR from tail DNA and by direct DNA sequencing. Expression of full-length mutant $Cybb^{C1024T}$ was confirmed by Western blot analysis. The transgenic mice were further backcrossed with the Cybb knockout mice to generate the $Cybb^{C1024T}$ transgenic mice on a Cybb knockout background.

C57BL/6 mice were used as wild-type (WT) mice and purchased from Animal Center, National Cheng Kung University (NCKU), Tainan, Taiwan. All mice were routinely backcrossed to the C57BL/6 background and underwent genome-wide genotyping to confirm the genetic background. Mice were housed in the animal facility of the Laboratory Animal Center at NCKU. All procedures were approved by the Institutional Animal Care and Use Committee of NCKU.

Example 2: Analysis of CGD Transgenic Mice

The expression of H338Y-gp91$^{phox}$ protein in neutrophils from the $Cybb^{C1024T}$ transgenic $Cybb^{-/-}$ mice was examined by SDS-PAGE and Western blotting with an anti-gp91$^{phox}$ antibody. To isolate neutrophils, mice were injected intraperitoneally with 3 ml of 3% thioglycollate to elicit peritoneal neutrophils. Four hours later, the mice were sacrificed, and the peritoneal cavity was washed twice with 5 ml of Hanks buffered salt solution (HBSS) with 2 mM ethylene glycol tetraacetic acid to collect the elicited peritoneal neutrophils. Peritoneal neutrophils were then washed with PBS before use.

The results indicated that neutrophils isolated from $Cybb^{C1024T}$ transgenic $Cybb^{-/-}$ mice produced the underglycosylated form of H338Y-gp91$^{phox}$. The levels of the glycosylated form of H338Y-gp91$^{phox}$ protein were significantly lower in $Cybb^{C1024T}$ transgenic $Cybb^{-/-}$ mice as compared to wild-type mice. As expected, gp91$^{phox}$ expression in $Cybb^{-/-}$ mice was not detected. These results indicate that a murine model of CGD was successfully established carrying the $Cybb^{C1024T}$ mutation and demonstrating trafficking-defective H338Y-gp91$^{phox}$ protein expression that mimics that seen in human CGD patients.

Example 3: Production of Curcumin-Loaded Nanoparticles

Curcumin-loaded poly(lactic-co-glycolic acid) (PLGA) nanoparticles were prepared with a modified approach of double emulsification (W1/O/W2 emulsion; see Zhong et al. 2010, J. Nanobiotechnology 8:6). Briefly, curcumin was dissolved in 500 μL of alcohol (W1) while PLGA (PLA: PGA=50:50, MW=60,000) was dispersed in dichloromethane (O). W1 was added to O and mixed with a probe-type ultrasonic vibrator to form a first emulsion. The first emulsion, i.e., W1/O, was added to a 1% polyvinyl alcohol (PVA) aqueous solution (W2) and agitated to form a second emulsion (W1/O/W2) containing PLGA nanoparticles. The second emulsion was then degassed under vacuum to remove the organic solvents, and any free curcumin and PVA remaining were removed by centrifugation. The PLGA nanoparticles were analyzed for average loading capacity by measuring optical density at 435 nm using a NanoDrop 1000™ (NanoDrop Technologies, LLC, USA).

Example 4: Production of ER-Targeted Curcumin-Loaded Nanoparticles

The curcumin-loaded PLGA nanoparticles produced as described in the preceding paragraph were conjugated to an ER-targeting peptide as follows. The curcumin-loaded PLGA nanoparticles were incubated in an ethyldimethylaminopropyl carbodiimide/N-hydroxysuccinimide solution for 1 h and then removed from the solution. The curcumin-loaded PLGA nanoparticles were suspended in H$_2$O together with a 10-fold molar excess of the ER-targeting peptide KDEL and incubated for 18 hours, after which excess peptide was removed by centrifugation. The labeled nanoparticles were re-dispersed in a phosphate-buffered saline (PBS) solution.

Example 5: Treatment of $Cybb^{C1024T}$ Transgenic $Cybb^{-/-}$ Mice with Curcumin-Loaded Nanoparticles Curcumin-loaded PLGA nanoparticles with or without the ER-targeting KDEL peptide were tested for their effects on the expression and maturation of H338Y-gp91$^{phox}$ protein in $Cybb^{C1024T}$ transgenic $Cybb^{-/-}$ mice. Briefly, mice were untreated or treated separately with free curcumin, curcumin-loaded PLGA nanoparticles, or curcumin-loaded ER-targeted PLGA nanoparticles for 24 hours in amounts corresponding to 20 mg/kg of curcumin. Neutrophils from the mice were elicited, isolated, and analyzed for expression of H338Y-gp91$^{phox}$ protein as described above.

Statistical analyses were carried out with Prism software (GraphPad Software). The mean values from each group are presented as mean±SEM and compared by using one-way analysis of variance (ANOVA) followed by a post hoc least significant difference test or two-way ANOVA followed by Bonferroni post hoc test. In all experiments, p-values of less than 0.05 were considered statistically significant.

Figure 1A:
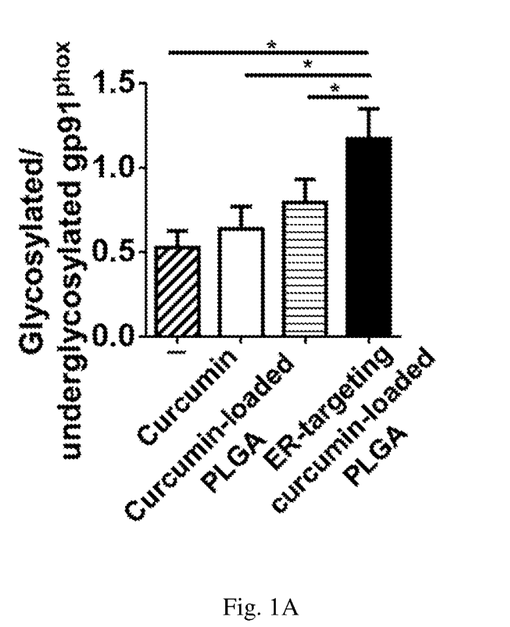
FIG. 1A is a bar graph showing the ratio between glycosylated and under-glycosylated forms of $gp91^{phox}$ in $Cybb^{C1024T}$ transgenic mice on a $Cybb^{-/-}$ background ("TG mice") determined by Western Blot analysis of neutrophils isolated from untreated mice (-), mice treated with free curcumin, or treated with the indicated curcumin-loaded PLGA nanoparticles (n=4; *: p<0.05)

The results showed that all treated and untreated $Cybb^{C1024T}$ transgenic $Cybb^{-/-}$ mice expressed the underglycosylated form of H338Y-gp91$^{phox}$. Mice treated with free curcumin did not show any change in the amount of glycosylated H338Y-gp91$^{phox}$ expressed as compared to untreated mice. On the other hand, mice treated with curcumin-loaded PLGA nanoparticles showed a 1.3-fold increase in expression of glycosylated H338Y-gp91$^{phox}$ as compared to untreated mice. Further, mice treated with curcumin-loaded ER-targeted PLGA nanoparticles expressed 1.7-fold more glycosylated H338Y-gp91$^{phox}$ as compared to untreated mice. A similar result was obtained upon analyzing the ratios of glycosylated versus underglycosylated H338Y-gp91$^{phox}$ in the same samples. See FIG. 1A.

These data show that delivering curcumin to the ER via an ER-targeted PLGA nanoparticle in $Cybb^{C1024T}$ transgenic $Cybb^{-/-}$ mice facilitates the maturation of mutant H338Y-gp91$^{phox}$ protein in neutrophils.

Example 6: Reactive Oxygen Species Production in $Cybb^{C1024T}$ Transgenic $Cybb^{-/-}$ Mice As mentioned above, production of reactive oxygen species (ROS) by NOX2 activity in neutrophils, which is essential for bacterial clearance, is compromised in CGD patients as a result of the sequestration of gp91$^{phox}$ in the ER. NOX2 function in $Cybb^{C1024T}$ transgenic $Cybb^{-/-}$ mice was examined by measuring ROS production in neutrophils from these mice treated with free curcumin or treated with curcumin-loaded ER-targeted PLGA nanoparticles.

Figure 1B:
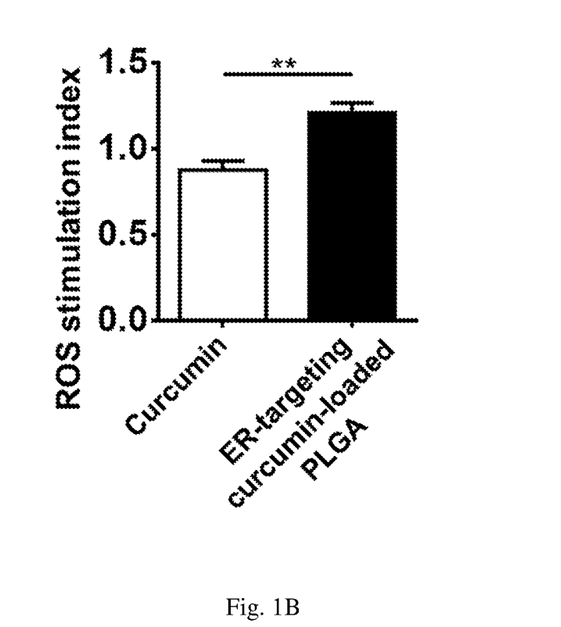
FIG. 1B, is a bar graph showing reactive oxygen species (ROS) generation in neutrophils isolated from TG mice treated with free curcumin or with ER-targeting curcumin-loaded PLGA nanoparticles (n=4; **: p<0.01)

ROS production assay Peritoneal neutrophils from $Cybb^{C1024T}$ transgenic $Cybb^{-/-}$ mice were elicited and isolated as described above. The neutrophils were washed with 1×HBSS and 5% FBS three times and then incubated with 10 μM 2',7'-dichlorodihydrofluorescein diacetate at 37° C.

for 30 min. Cells were then incubated with 100 ng/ml phorbol myristate 13-acetate (Sigma) at 37° C. for 15 min. to induce ROS production. Fluorescence in PMA-treated cells was detected by flow cytometry using a FACSCalibur instrument (BD Biosciences) and the data was analyzed with Flowing Software 2 software. The results are shown in FIG. 1B.

ROS production by neutrophils isolated from $Cybb^{C1024T}$ transgenic $Cybb^{-/-}$ mice treated with curcumin-loaded ER-targeted PLGA nanoparticles was significantly higher than that isolated from free curcumin-treated animals. These data show that delivering curcumin to the ER via an ER-targeted PLGA nanoparticle in $Cybb^{C1024T}$ transgenic $Cybb^{-/-}$ mice restores NOX2 function in neutrophils and correlates with the ability of ER-delivered curcumin to facilitate maturation of mutant H338Y-gp91$^{phox}$ protein in neutrophils.

Example 7: Peritoneal Bacterial Clearance Test

NOX2 function is also necessary to clear bacterial infections. Bacterial clearance was examined by intraperitoneal injection of bacteria, i.e., *S. aureus*, into untreated $Cybb^{C1024T}$ transgenic $Cybb^{-/-}$ mice, transgenic mice treated with curcumin, and transgenic mice treated with PLGA-encapsulated curcumin.

Bacteria Preparation

*S. aureus* (ATCC No. 25923) was cultured overnight at 37° C. on a tryptic soy agar plate with 10% sheep blood. A single colony was picked from the plate and sub-cultured in Luria-Bertani medium (LB) at 37° C. for 16 h. The bacterial culture was diluted 1:50 with 5 mL LB and incubated at 37° C. for 6 h. Colony forming units (CFU) in the *S. aureus* culture was determined by spreading a 10 μl drop of the culture on a TSA plate, incubating the plate overnight, and counting the number of colonies.

Treatment of Mice with *S. aureus*

$Cybb^{C1024T}$ transgenic $Cybb^{-/-}$ mice were left untreated or were treated for 24 h with 20 mg/kg free curcumin, curcumin-loaded PLGA nanoparticles, or curcumin-loaded ER-targeted PLGA nanoparticles as set forth above. Mice were injected intraperitoneally with 1×10$^7$ CFU of *S. aureus* in 100 μl PBS. After 4 h, mice were sacrificed and peritoneal cells were harvested via lavage with 5 ml of PBS. CFU of *S. aureus* in the lavage fluid was determined by plating a 50 μl drop of lavage fluid on TSA plates and counting *S. aureus* colonies growing after an overnight incubation.

Figure 1C:
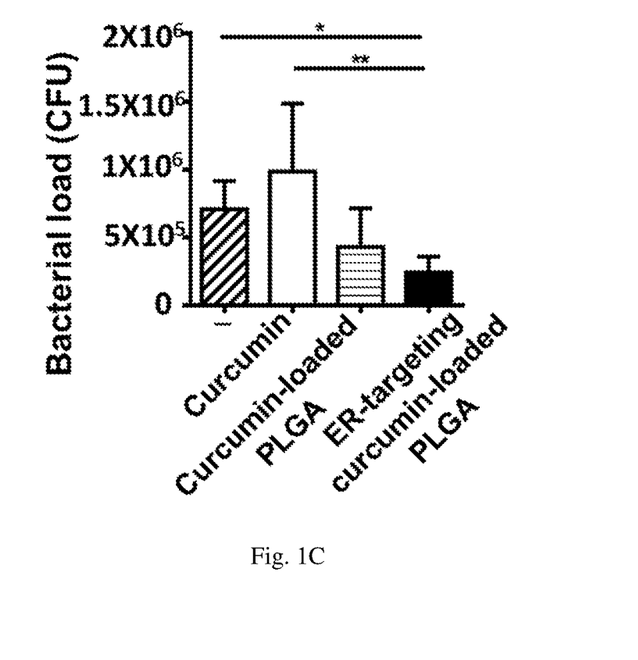
FIG. 1C is a bar graph showing bacterial load as colony forming units (CFU) in TG mice untreated (-) and treated as indicated. (n=4; *: p<0.05; **: p<0.01)

The results, shown in FIG. 1C, indicated that the bacterial load in mice treated with curcumin-loaded ER-targeted PLGA nanoparticles were significantly lower than that in untreated mice, and were also lower than that in mice treated with free curcumin or with non-targeted curcumin-loaded PLGA nanoparticles.

Following above procedures, it was determined that there were no significant differences in the percentages of thioglycollate-elicited neutrophils in peritoneal exudates isolated from mice treated with free curcumin, curcumin-loaded PLGA nanoparticles, or curcumin-loaded ER-targeted PLGA nanoparticles.

These findings, taken together, show that delivering curcumin to the ER via an ER-targeted PLGA nanoparticle in $Cybb^{C1024T}$ transgenic $Cybb^{-/-}$ mice restores the anti-bacterial function of neutrophils.

Example 8: Quantification of ER Targeting of PLGA Nanoparticles

Intracellular distribution in cells treated with curcumin-loaded PLGA nanoparticles with or without ER-targeting peptide decoration, was measured by immunostaining and co-localization in differentiated HL-60 cells, which have many characteristics of neutrophils.

Differentiation of HL-60 Cells

HL-60 cells were cultured at 37° C. in RPMI 1640 supplemented with 10% heat-inactivated fetal bovine serum. Cells at a density of 3×10$^5$ cells/ml were treated with 1.3% dimethyl sulfoxide (Sigma-Aldrich) to induce differentiation. After 4 days of incubation, differentiated cells were harvested, and dead cells were removed by centrifugation through Ficoll-Hypaque.

Determination of subcellular localization of nanoparticles

Figure 2:
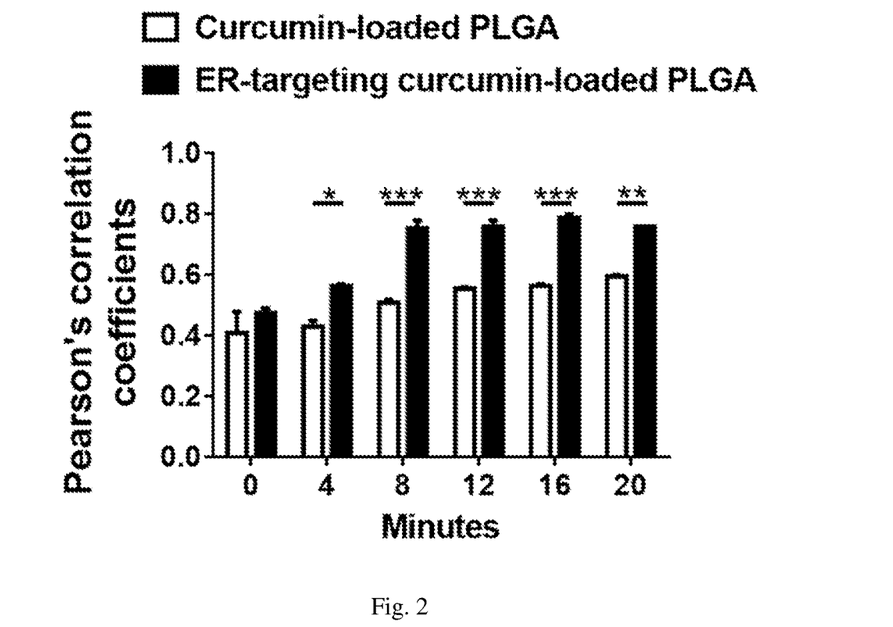
FIG. 2 is a bar graph quantifying co-localization over time of ER-targeting curcumin PLGA nanoparticles to the ER, as compared to non-targeted curcumin-loaded PLGA nanoparticles (*: p<0.05; : p<0.01; *: p<0.001)

Differentiated HL-60 cells were seeded on 8-well slides and then labeled with ER-Tracker, a cell-permeant fluorescent dye that localizes to the ER. Labeled cells were then treated with 10 μM curcumin-loaded PLGA nanoparticles or with 10 μM curcumin-loaded ER-targeted PLGA nanoparticles. Time-lapse fluorescence images were captured by confocal microscopy using excitation wavelengths of 488 nm and 374 nm, wavelengths that stimulates fluorescence of curcumin and the ER-Tracker dye, respectively. The degree of co-localization of the ER-tracker dye with the curcumin nanoparticles was calculated by Pearson's correlation method from the time-lapse images. The results are shown in FIG. 2.

The data showed that the ER-targeted nanoparticles were significantly localized to the ER within 4 min. of addition to the cells, as compared to non-targeted nanoparticles. See FIG. 2. This significant difference in localization increased over a 20 min. time period after addition of the nanoparticles. The results confirmed that the ER-targeted nanoparticles were indeed preferentially localized with the ER in living cells.

Example 9: Determination of Curcumin-Induced Intracellular Calcium Release

SERCA inhibitors such as curcumin cause an increase in intracellular calcium release from the ER. The ability of curcumin to induce calcium release was compared to that of PLGA nanoparticle-encapsulated curcumin.

Differentiated HL-60 cells were seeded on 8-well slides in calcium-free medium and loaded with the intracellular calcium-sensitive indicator dye Fluo-4AM. Cells were treated with thapsigargin (positive control) or treated with 0.5, 1, or 10 μM curcumin, curcumin-loaded PLGA nanoparticles, or curcumin-loaded ER-targeted PLGA nanoparticles. Fluorescence intensity over time was measured in treated cells by confocal microscopy and analyzed using ImageJ software. The change in fluorescence intensity over time divided by the baseline fluorescence intensity prior to calcium addition (ΔF/FO) was plotted versus time.

Treatment of cells with 10 μM free curcumin induced a significantly higher level of calcium release at a faster rate, as compared to treatment with 0.5 μM and 1 μM free curcumin. More specifically, the calcium levels in cells 40, 50, and 60 s after treatment with 10 μM free curcumin were significantly higher than those at the same time points in the cells treated with 0.5 μM or 1 μM free curcumin. The rate of intracellular calcium increase, derived from fluorescence versus time curves, was also highest in cells treated with 10 μM free curcumin, as compared to cells treated with lower concentrations of free curcumin.

Figure 3:
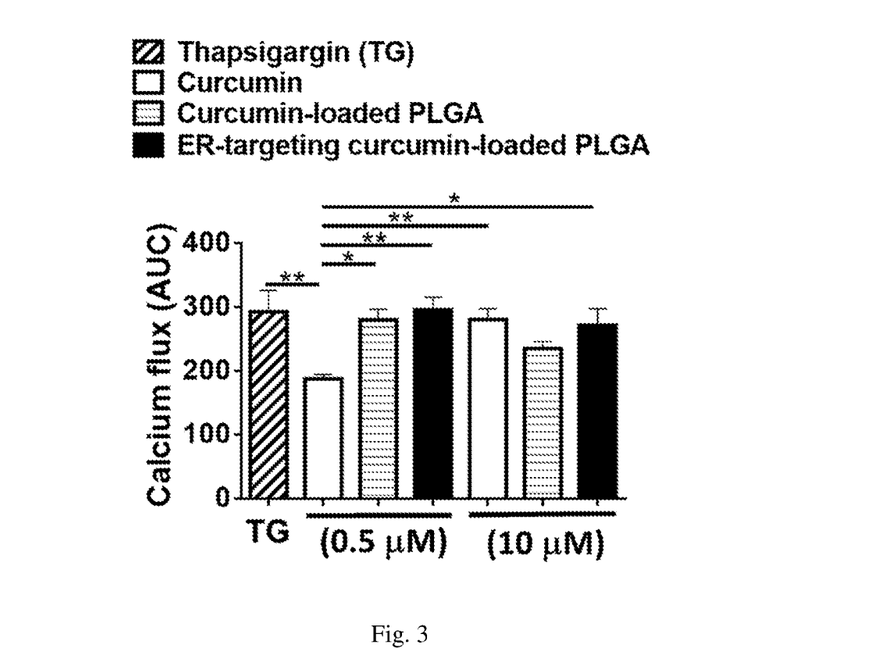
FIG. 3 is a bar graph showing calcium flux in differentiated HL60 cells treated as indicated calculated as area under the curve (AUC) from plots of intracellular calcium release rates versus time (n=4; *: p<0.05; : p<0.01; *: p<0.001)

Calcium release was also measured in cells treated with curcumin-loaded PLGA nanoparticles and curcumin-loaded ER-targeted PLGA nanoparticles. The data showed that treating differentiated HL-60 cells with 0.5 μM and 1 μM of either of these nanoparticles induced an elevation of intracellular calcium level and a rate of increase similar to those induced by 10 µM free curcumin treatment. The overall calcium flux indicated as area under the curves (AUC) is shown in FIG. 3.

The results show that curcumin-loaded PLGA nanoparticles and ER-targeting curcumin-loaded PLGA nanoparticles at 0.5 µM were capable of elevating the intracellular calcium levels to the same level of thapsigargin treatment. Increasing the curcumin nanoparticle concentration to 10 µM did not further increase the peak level or rate of increase in intracellular calcium level in the treated cells.

Example 10: Determination of Curcumin-Induced Extracellular Calcium Influx

Extracellular calcium influx, which is triggered by the depletion of ER calcium stores, was measured in cells treated with free curcumin or treated with curcumin-loaded nanoparticles as follows.

Differentiated HL-60 cells were pretreated with free curcumin (10 µM), curcumin-loaded PLGA nanoparticles (0.5 µM), and curcumin-loaded ER-targeted PLGA nanoparticles (0.5 µM) at 37° C. overnight. Cells were washed with calcium-free HBSS, seeded on poly-lysine coated 8-well slides (ibidi, Planegg, Germany) at a density of $1 \times 10^6$ cells/ml, and incubated at 37° C. for 30 min. Cells were labeled with 2 µM of the calcium-sensitive fluorescent dye Fluo-4 AM and 1 µM of ER-tracker at 37° C. for 30 min. Labeled cells were treated with 1.25 mM $CaCl_2$.

Figure 4:
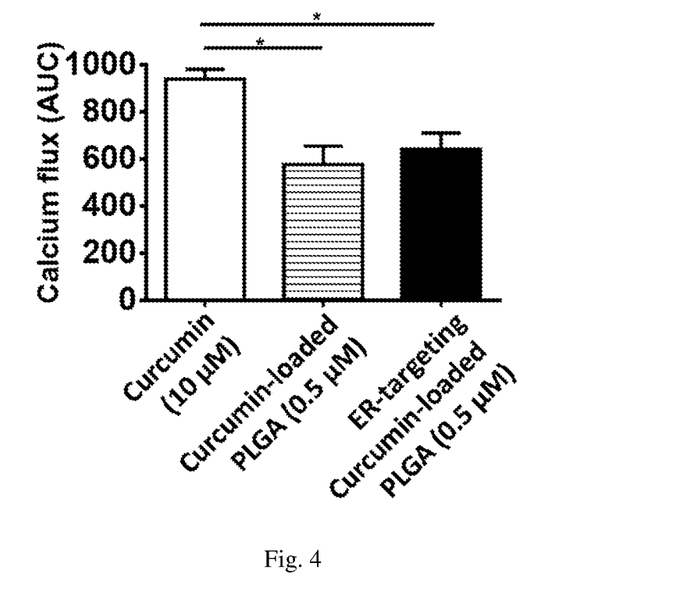
FIG. 4 is a bar graph showing calcium flux in differentiated HL60 cells treated as indicated calculated as area under the curve (AUC) from plots of extracellular calcium uptake rates versus time (n=3; *: p<0.05)

Fluorescence images were captured by confocal microscopy every 10 s for 5 min. following the addition of $CaCl_2$. Fluorescence intensities in these images were analyzed using ImageJ software. The change in fluorescence intensity over time divided by the baseline fluorescence intensity prior to calcium addition (ΔF/FO) was plotted versus time, and the rate of calcium level increase (ΔF/F/s) was derived from that plot. The overall calcium flux was calculated as the area under the curve (AUC) of a ΔF/F/s versus time curve. The results are shown in FIG. 4.

The addition of 1.25 mM extracellular calcium did not induce significant calcium influx in untreated cells. Thapsigargin, a SERCA inhibitor used as a positive control, induced calcium influx within 10 s after addition.

Free curcumin at 10 µM induced early extracellular calcium influx similar to that induced by thapsigargin. By contrast, extracellular calcium entry induced by 0.5 µM curcumin-loaded PLGA nanoparticles and 0.5 µM curcumin-loaded ER-targeted PLGA nanoparticles was only detected 60 seconds after treatment with these nanoparticles.

Measurement of rates of fluorescence intensity increase revealed that treatment of cells with free curcumin induced a more significant calcium influx at an earlier time point, as compared to curcumin-loaded nanoparticles. In particular, the calcium influx rate 20 s after treatment with 10 µM of free curcumin was significantly higher than that in cells treated with 0.5 µM of curcumin-loaded PLGA nanoparticles or with 0.5 µM of curcumin-loaded ER-targeted.

The delay in extracellular calcium entry induced by PLGA nanoparticle-encapsulated curcumin reduced the overall calcium influx in comparison with the extracellular calcium influx induced by free curcumin. See FIG. 4. This result was unexpected, in view of the fact that free curcumin induced similar levels of ER calcium depletion as compared to curcumin loaded in PLGA nanoparticles. As pointed out above, depletion of ER calcium triggers extracellular calcium influx.

Example 11: Effect of Curcumin on ER Stress and Cell Survival

As mentioned above, it has been shown that curcumin is cytotoxic, as it induces ER stress and apoptosis. The cytotoxicity of free curcumin was compared to that of encapsulated curcumin by measuring in treated cells mitochondrial membrane potential (one measure of cytotoxicity), apoptotic markers, and ER stress-related protein expression.

Measurement of Mitochondrial Membrane Potential

Differentiated HL-60 cells were treated with 0.5 µM or 10 µM free curcumin, curcumin-loaded PLGA nanoparticles, or curcumin-loaded ER-targeted PLGA nanoparticles for 24 hours. Treated cells were labeled with 250 nM of the mitochondrial membrane potential indicator dye tetramethylrhodamine (TMRM) at 37° C. for 30 min. TMRM-labeled cells were analyzed by flow cytometry and their mitochondrial membrane potentials quantified using the Flowing Software 2 software package.

Figure 5A:
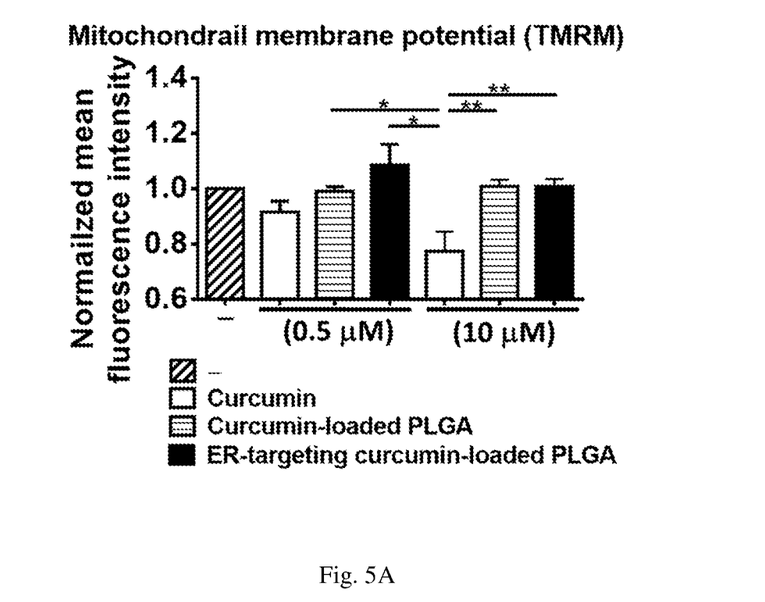
FIG. 5A is a bar graph of mitochondrial membrane potential determined with a fluorescent dye in differentiated HL60 cells treated as indicated (n=4; *: p<0.05; **: p<0.01)

The results revealed that cells treated with 10 µM free curcumin showed a significant reduction in mitochondrial membrane potential as compared to control untreated cells. See FIG. 5A. By contrast, mitochondrial membrane potential in cells treated with 10 µM curcumin-loaded PLGA nanoparticles or 10 µM curcumin-loaded ER-targeted PLGA nanoparticles was not different from control untreated cells and was significantly higher when compared to free curcumin-treated cells. See Id.

Detection of Apoptotic Cells

Cells treated as above with free or encapsulated curcumin were washed with ice-cold phosphate-buffered saline and stained with phycoerythrin-Annexin V and 7 amino-actinomycin D (7-AAD) at room temperature for 15 min. Annexin V binds to the surface of cells undergoing apoptosis, and 7-AAD only enters and stains apoptotic cells. Stained cells were subjected to flow cytometry analysis and the results analyzed using the Flowing Software 2 analysis package.

Figure 5B:
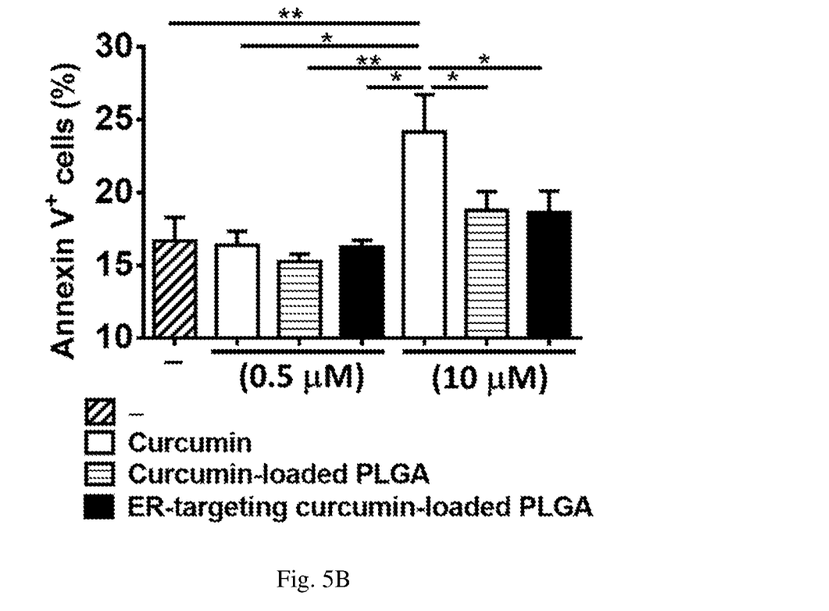
FIG. 5B is a bar graph of the percentage of annexin V positive cells determined by flow cytometry of differentiated HL60 cell populations treated as indicated (n=4; *: p<0.05; **: p<0.01)

The results showed a significant increase in the number of apoptotic cells after treatment with 10 µM free curcumin, as measured by Annexin V binding to the cell surface. See FIG. 5B. Cells treated with the same concentration of curcumin-loaded PLGA nanoparticles or curcumin-loaded ER-targeted PLGA nanoparticles showed significantly lower numbers of apoptotic cells. See Id.

ER Stress Response

To determine whether the activation of the ER stress response is involved in curcumin-induced apoptosis, the levels of ER stress markers Bip and phosphorylated ERK, as well as the level of cleaved Caspase-3, a marker of apoptosis, were quantified by Western blot analysis of cells treated with 10 µM curcumin or encapsulated curcumin.

Briefly, treated cells were lysed in 100 µl of lysis buffer (1% Triton-X100, 150 mM NaCl, 10 mM Tris base, 1 mM EDTA, 1 mM EGTA, 50×protease inhibitor cocktail, pH 7.4). Lysed samples were subjected to 10% SDS-PAGE and transferred to membranes for Western Blot analysis using antibodies that bind to Bip, phospho-ERK, total ERK, cleaved caspase-3, and β-actin. Binding of these antibodies was visualized using commercially available enhanced chemiluminescence reagents. Chemiluminescent signals were quantified from images using ImageJ software.

Figure 5C:
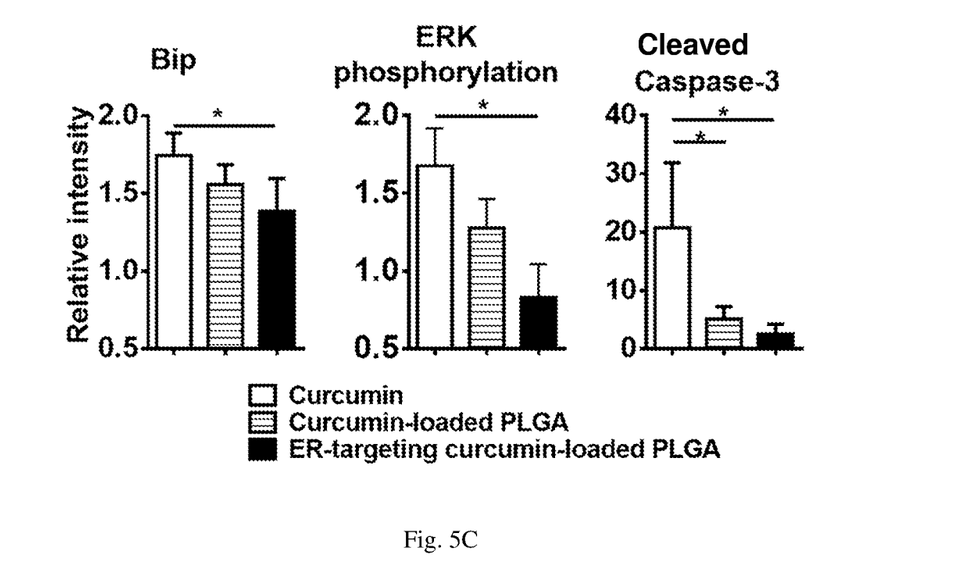
FIG. 5C shows bar graphs of relative intensity of Bip (left panel), phosphorylated ERK (center panel), and cleaved caspase-3 (right panel), measured from Western Blot analysis of protein extracted from differentiated HL60 cells treated as indicated (n=4; *: p<0.05)

The data showed that treatment of cells with free curcumin and curcumin-loaded PLGA nanoparticles increased Bip expression and ERK phosphorylation, as compared to untreated control cells. Unexpectedly, Bip expression and ERK phosphorylation in cells treated with curcumin-loaded ER targeted PLGA nanoparticles was significantly lower than in free curcumin-treated cells. See FIG. 5C, left and center panels.

Measurements of caspase-3 cleavage revealed that PLGA nanoparticle-encapsulated curcumin induced significantly less caspase-3 cleavage as compared to treatment with free curcumin. See FIG. 5C, right panel.

In sum, the findings set forth in the examples, supra, indicate that free curcumin at a concentration that can inhibit SERCA, i.e., 10 μM, induces a rapid calcium influx, leading to mitochondrial damage, ER stress, and induction of apoptosis. PLGA nanoparticle-encapsulated curcumin having equivalent SERCA inhibitory activity induces delayed calcium influx and protects cells from mitochondrial damage, ER stress, and apoptosis.

Further, curcumin-loaded ER-targeted PLGA nanoparticles, by inhibiting SERCA, successfully releases H338Y-gp91$^{phox}$ sequestered in the ER, thereby recovering NOX2 function without excessive damage to cell viability.

Example 12: Effect of Curcumin on Erythroblast Differentiation

Erythroblast differentiation was measured in human peripheral blood hematopoietic cells (HSCs) treated with free curcumin or treated with curcumin-loaded nanoparticles as follows.

Human CD34$^+$ HSCs were cultured in Iscove's modified Dulbecco medium containing 15% heat-inactivated fetal calf serum, 2 U/ml of recombinant human erythropoietin, 20 ng/ml of stem cell factor, and 10 ng/ml of interleukin-3 (IL-3). On day 4, the medium was replaced with fresh medium without IL-3 and the HSCs were cultured for another 5 days.

Figure 6A:
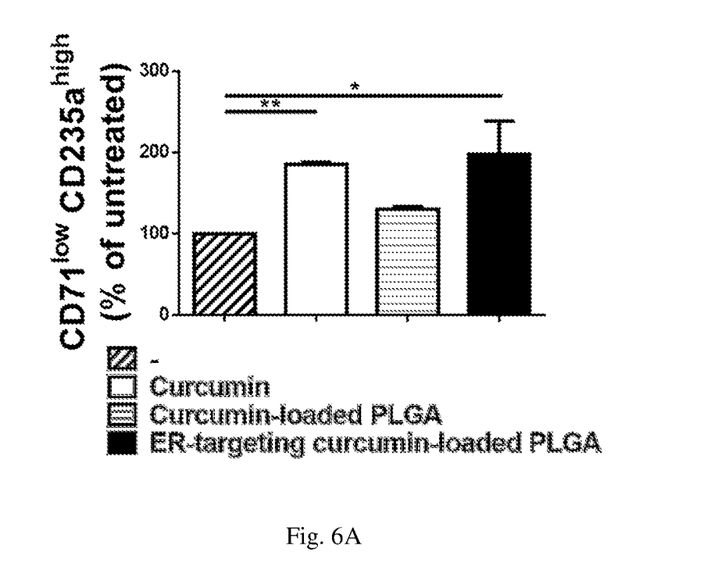
FIG. 6A is a bar graph showing numbers of $CD71^{low}$ $CD235a^{high}$ cells as a percentage of untreated determined by flow cytometry of human peripheral blood hematopoietic cells (HSC) untreated (-) and treated as indicated (n=3; *: p<0.05; : p<0.01)

The maturation of erythroblasts was analyzed by detecting the surface expression of CD71 and CD235a with flow cytometry. The results are shown in FIG. 6A. The data showed that free curcumin and ER-targeting curcumin-loaded PLGA nanoparticles significantly enhanced the percentages of more mature CD71$^{low}$ CD235$^{high}$ cells in treated HSCs.

Figure 6B:
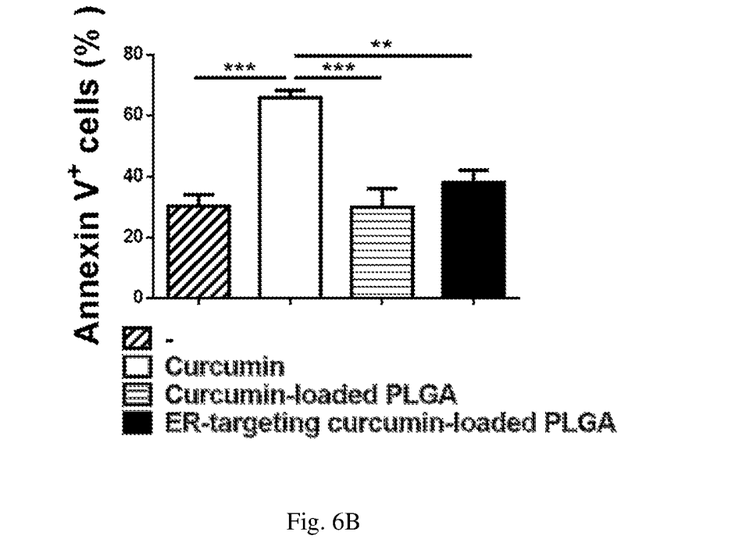
FIG. 6B is a bar graph of the percentage of annexin V positive cells determined by flow cytometry of HSC treated as indicated (n=3; : p<0.01; ***: p<0.001).

Measurement of Annexin V-positive cells revealed that ER-targeting PLGA nanoparticle-encapsulated curcumin induced significantly less apoptosis in treated HSC, as compared to treatment with free curcumin. See FIG. 6B.

In sum, treating HSCs with ER-targeting curcumin-loaded PLGA nanoparticles promotes erythroblast maturation and, at the same time, prevents curcumin-induced apoptosis.

Other Embodiments

All of the features disclosed in this specification may be combined in any combination. Each feature disclosed in this specification may be replaced by an alternative feature serving the same, equivalent, or similar purpose. Unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating a disease caused by protein retention in the endoplasmic reticulum, the method comprising:

obtaining a sarcoplasmic/endoplasmic reticulum calcium ATPase (SERCA) pump inhibitor encapsulated in a polymer nanoparticle, and administering an effective amount of the inhibitor to a subject in need thereof, wherein the inhibitor is curcumin, the polymer is poly(lactic-co-glycolic acid), the polymer nanoparticle is surface-modified with peptide KDEL (SEQ ID NO: 1) conjugated to the polymer such that the polymer nanoparticle is targeted to the endoplasmic reticulum (ER), the effective amount of the inhibitor reduces protein retention in the ER, and the encapsulation lowers side effects of the inhibitor as compared to administering the inhibitor without encapsulation.

2. The method of claim 1, wherein the side effects are ER stress or apoptosis.

3. The method of claim 1, wherein the disease is chronic granulomatous disease, cystic fibrosis, hereditary emphysema, hereditary hemochromatosis, oculocutaneous albinism, protein C deficiency, type I hereditary angioedema, Fabri disease, Tay-Sachs disease, congenital sucrase-isomaltase deficiency, CriglerNajjar type 2, diabetes mellitus, Laron syndrome, primary hypothyroidism, congenital long QT syndrome, thyroxine binding globulin deficiency, β-thalassemia/Hb E disease, familial hypercholesterolemia, familial chylomicronemia, abeta-lipoproteinema, congenital hypothyroidism, osteogenesis imperfecta, osteopetrosis, hereditary hypofibrinogenemia, nephrogenic diabetes insipidus, neurohypophyseal diabetes insipidus, Charcot-Marie-Tooth disease, Pelizaeus-Merzbacher disease, Alzheimer's disease, von Willebrand disease type IIA, Tangier disease, or hereditary hemorrhagic telangiectasia type 2 with ALK1 missense mutation.

4. The method of claim 3, wherein the disease is chronic granulomatous disease.

5. The method of claim 1, wherein the effective amount of the inhibitor enhances reactive oxygen species generation by leukocytes in the subject.

6. The method of claim 5, wherein the effective amount of the inhibitor enhances peritoneal bacterial clearance mediated by the leukocytes.

7. A pharmaceutical composition, comprising curcumin encapsulated in a poly(lactic-co-glycolic acid) polymer nanoparticle and a pharmaceutically acceptable carrier, wherein the polymer nanoparticle is surface-modified with peptide KDEL (SEQ ID NO: 1) such that the polymer nanoparticle is targeted to the endoplasmic reticulum.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: ER targetting peptide

<400> SEQUENCE: 1

Lys Asp Glu Leu
1

<210> SEQ ID NO 2
<211> LENGTH: 4
<212> TYPE: PRT
<213> ORGANISM: Artificial Sequence
<220> FEATURE:
<223> OTHER INFORMATION: ER targetting peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 2

Lys Lys Xaa Xaa
1
```